(12) United States Patent
Saar et al.

(10) Patent No.: US 11,273,031 B2
(45) Date of Patent: Mar. 15, 2022

(54) PROSTHETIC HEART VALVE WITH REDUCED STITCHING

(71) Applicant: Edwards Lifesciences Corporation, Irvine, CA (US)

(72) Inventors: Tomer Saar, Pardes Hanna-Karkur (IL); Michael Bukin, Pardes Hanna (IL); Elena Sherman, Pardes Hana (IL); Alexander Barash, Tzoran (IL); Yana Mayatskaya, Or-Aqiva (IL)

(73) Assignee: Edwards Lifesciences Corporation, Irvine, CA (US)

( * ) Notice: Subject to any disclaimer, the term of this patent is extended or adjusted under 35 U.S.C. 154(b) by 200 days.

(21) Appl. No.: 16/799,741

(22) Filed: Feb. 24, 2020

(65) Prior Publication Data
US 2020/0205964 A1    Jul. 2, 2020

Related U.S. Application Data

(63) Continuation of application No. 15/709,355, filed on Sep. 19, 2017, now Pat. No. 10,575,944.
(Continued)

(51) Int. Cl.
*A61F 2/24*    (2006.01)

(52) U.S. Cl.
CPC .......... *A61F 2/2418* (2013.01); *A61F 2/2412* (2013.01); *A61F 2210/0014* (2013.01); *A61F 2220/0075* (2013.01)

(58) Field of Classification Search
CPC .............................. A61F 2/2412; A61F 2/2418
See application file for complete search history.

(56) References Cited

U.S. PATENT DOCUMENTS

| 3,755,823 A | 9/1973 | Hancock |
| 4,035,849 A | 7/1977 | Angell et al. |

(Continued)

FOREIGN PATENT DOCUMENTS

| DE | 19532846 A1 | 3/1997 |
| DE | 19546692 A1 | 6/1997 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Suba Ganesan
(74) *Attorney, Agent, or Firm* — Klarquist Sparkman, LLP; Joel B. German

(57) ABSTRACT

An implantable prosthetic valve that is radially collapsible to a collapsed configuration and radially expandable to an expanded configuration includes an annular frame including a plurality of angled strut members, and a skirt member secured to the frame. The skirt member includes a plurality of extension portions wrapped around at least one strut member adjacent the extension portions. The prosthetic valve further includes a cord member threaded through at least a portion of the plurality of extension portions to secure the skirt member to the at least one strut member.

20 Claims, 11 Drawing Sheets

Related U.S. Application Data

(60) Provisional application No. 62/398,439, filed on Sep. 22, 2016.

(56) References Cited

U.S. PATENT DOCUMENTS

| | | | |
|---|---|---|---|
| 4,777,951 A | 10/1988 | Cribier et al. |
| 4,787,899 A | 11/1988 | Lazarus |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,282,847 A | 2/1994 | Trescony et al. |
| 5,370,685 A | 12/1994 | Stevens |
| 5,411,552 A | 5/1995 | Andersen et al. |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,665,115 A | 9/1997 | Cragg |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,925,063 A | 7/1999 | Khosravi |
| 6,027,525 A | 2/2000 | Suh et al. |
| 6,168,614 B1 | 1/2001 | Andersen et al. |
| 6,221,091 B1 | 4/2001 | Khosravi |
| 6,245,102 B1 | 6/2001 | Jayaraman |
| 6,302,906 B1 | 10/2001 | Goicoechea et al. |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,767,362 B2 | 7/2004 | Schreck |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,018,408 B2 | 3/2006 | Bailey et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,655,034 B2 | 2/2010 | Mitchell et al. |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,449,606 B2 | 5/2013 | Eliasen et al. |
| 8,652,203 B2 | 2/2014 | Quadri et al. |
| 2002/0026094 A1 | 2/2002 | Roth |
| 2002/0032481 A1 | 3/2002 | Gabbay |
| 2002/0138135 A1 | 9/2002 | Duerig et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0075728 A1 | 4/2005 | Nguyen et al. |
| 2005/0096736 A1 | 5/2005 | Osse et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2006/0183383 A1 | 8/2006 | Asmus et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0265700 A1 | 11/2007 | Eliasen et al. |
| 2008/0071361 A1* | 3/2008 | Tuval ............... A61F 2/2409 623/2.1 |
| 2008/0114442 A1 | 5/2008 | Mitchell et al. |
| 2008/0125853 A1 | 5/2008 | Bailey et al. |
| 2009/0157175 A1* | 6/2009 | Benichou ............ A61F 2/2412 623/2.18 |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0168844 A1 | 7/2010 | Toomes et al. |
| 2010/0198347 A1 | 8/2010 | Zakay et al. |
| 2011/0015729 A1 | 1/2011 | Jimenez et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0190857 A1 | 7/2013 | Mitra et al. |
| 2013/0274873 A1 | 10/2013 | Delaloye et al. |
| 2013/0317598 A1 | 11/2013 | Rowe et al. |
| 2013/0331929 A1 | 12/2013 | Mitra et al. |
| 2014/0005777 A1* | 1/2014 | Anderl ............... A61F 2/2445 623/2.18 |
| 2014/0194981 A1 | 7/2014 | Menk et al. |
| 2014/0200661 A1 | 7/2014 | Pintor et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0173899 A1* | 6/2015 | Braido ............... A61F 2/2418 623/2.38 |
| 2016/0175095 A1 | 6/2016 | Dienno et al. |

FOREIGN PATENT DOCUMENTS

| | | |
|---|---|---|
| DE | 19857887 A1 | 7/2000 |
| DE | 19907646 A1 | 8/2000 |
| EP | 0103546 A1 | 3/1984 |
| EP | 0597967 A1 | 5/1994 |
| EP | 0592410 B1 | 10/1995 |
| EP | 0850607 A1 | 7/1998 |
| EP | 1796597 A2 | 6/2007 |
| FR | 2788217 A1 | 7/2000 |
| FR | 2815844 A1 | 5/2002 |
| SU | 1271508 A1 | 11/1986 |
| WO | 9117720 A1 | 11/1991 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0149213 A2 | 7/2001 |

(56) References Cited

FOREIGN PATENT DOCUMENTS

| WO | 0154625 | A1 | 8/2001 |
|---|---|---|---|
| WO | 0162189 | A1 | 8/2001 |
| WO | 0164137 | A1 | 9/2001 |
| WO | 0176510 | A2 | 10/2001 |
| WO | 0222054 | A1 | 3/2002 |
| WO | 0236048 | A1 | 5/2002 |
| WO | 0247575 | A2 | 6/2002 |
| WO | 03047468 | A1 | 6/2003 |
| WO | 2005034812 | | 4/2005 |
| WO | 2005084595 | A1 | 9/2005 |
| WO | 2006111391 | A1 | 10/2006 |
| WO | 2006127089 | A1 | 11/2006 |
| WO | 2006138173 | A2 | 12/2006 |
| WO | 2005102015 | A3 | 4/2007 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008091515 | A2 | 7/2008 |
| WO | 2009033469 | A1 | 3/2009 |
| WO | 2010121076 | A2 | 10/2010 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

\* cited by examiner

PROSTHETIC HEART VALVE WITH REDUCED STITCHING

CROSS REFERENCE TO RELATED APPLICATION

This application is a continuation of U.S. patent application Ser. No. 15/709,355, filed Sep. 19, 2017, which claims the benefit of U.S. Provisional Application No. 62/398,439, filed Sep. 22, 2016. The disclosures of U.S. patent application Ser. No. 15/709,355 and U.S. Provisional Application No. 62/398,439 are incorporated herein by reference in their entirety.

FIELD

The present application concerns embodiments of a leaflet skirt member and methods of attaching the skirt member to the leaflets and frame of a transcatheter heart valve.

BACKGROUND

In a typical transcatheter heart valve, the leaflets of the valve are lined with a reinforcing strip and sutured to the strut members of the frame, or sutured directly to the strut members of the frame. This process is difficult and time-consuming, and results in increased labor and cost to manufacture a valve. Accordingly, improvements to devices and methods for securing a leaflet or leaflet assembly to a frame are desirable.

SUMMARY

Certain embodiments of the disclosure concern implantable prosthetic heart valves with leaflet-skirt assemblies. In a representative embodiment, an implantable prosthetic valve that is radially collapsible to a collapsed configuration and radially expandable to an expanded configuration comprises an annular frame including a plurality of angled strut members, and a skirt member secured to the frame. The skirt member includes a plurality of extension portions wrapped around at least one strut member adjacent the extension portions. The prosthetic valve further comprises a cord member threaded through at least a portion of the plurality of extension portions to secure the skirt member to the at least one strut member.

In another representative embodiment, a method comprises situating a skirt member adjacent a strut member of a frame of a prosthetic valve, the skirt member including a plurality of extension portions, and wrapping at least a portion of the plurality of extension portions around the strut member. The method further comprises threading a cord member through the extension portions wrapped around the strut member to secure the skirt member to the frame.

In another representative embodiment, an implantable prosthetic valve that is radially collapsible to a collapsed configuration and radially expandable to an expanded configuration comprises an annular frame including a plurality of angled strut members and a leaflet-skirt assembly situated within and secured to the frame. The leaflet-skirt assembly comprises a valve leaflet and a skirt member secured to an edge portion of the valve leaflet. The skirt member has first and second longitudinal edge portions, and a plurality of extension portions on at least one of the longitudinal edge portions. The extension portions define tubular portions. The extension portions of the skirt member are wrapped around the strut members to secure the leaflet-skirt assembly to the frame.

In another representative embodiment, a method comprises securing a skirt member to an edge of a valve leaflet to form a leaflet-skirt assembly. The skirt member includes first and second longitudinal edge portions and a plurality of extension portions along at least one of the longitudinal edge portions. The extension portions define tubular portions. The method further comprises situating the leaflet-skirt assembly in a frame, and wrapping the extension portions of the skirt member around strut members of the frame to secure the leaflet-skirt assembly to the frame.

The foregoing and other objects, features, and advantages of the disclosed technology will become more apparent from the following detailed description, which proceeds with reference to the accompanying figures.

DETAILED DESCRIPTION

The present disclosure concerns embodiments of implantable prosthetic devices and, in particular, implantable prosthetic valves, and methods for making such devices. In particular embodiments, the prosthetic device comprises a prosthetic heart valve, and can be configured to be implanted in any of the native heart valves. In addition, the prosthetic heart valve can be, for example, a transcatheter heart valve, a surgical heart valve, or a minimally-invasive heart valve. The prosthetic valve also can comprise other types of valves implantable within other body lumens outside of the heart or heart valves that are implantable within the heart at locations other than the native valves, such as trans-atrial or trans-ventricle septum valves. In one aspect, a prosthetic heart valve includes one or more leaflet-skirt assemblies that allow the valve leaflets to be quickly and accurately secured to strut members of the frame without the need to suture the leaflets to the strut members, or with minimal suturing.

Figure 1:
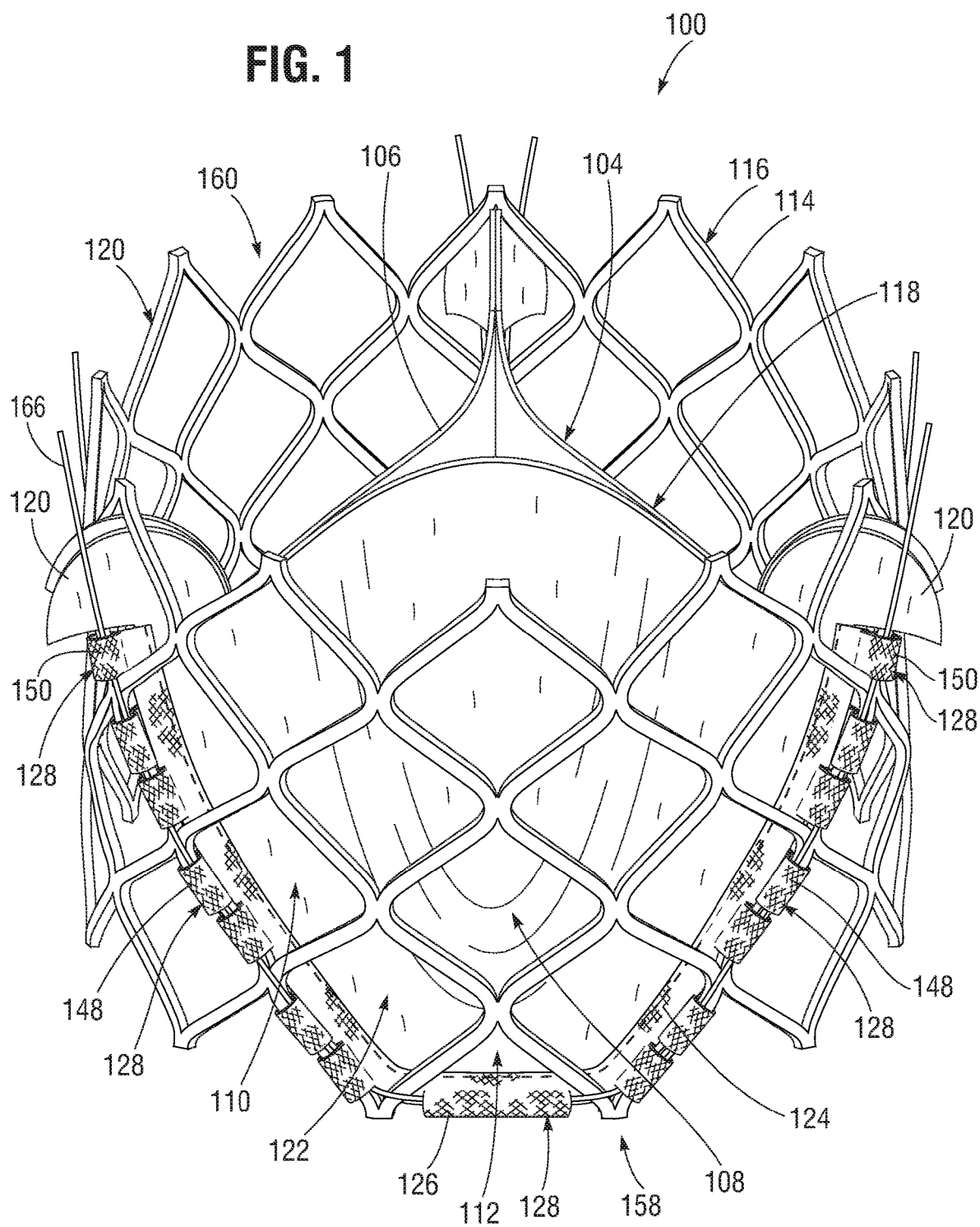
FIG. 1 is a perspective view of a representative embodiment of a frame for a prosthetic heart valve including a leaflet-skirt assembly secured thereto.
Figure 11:
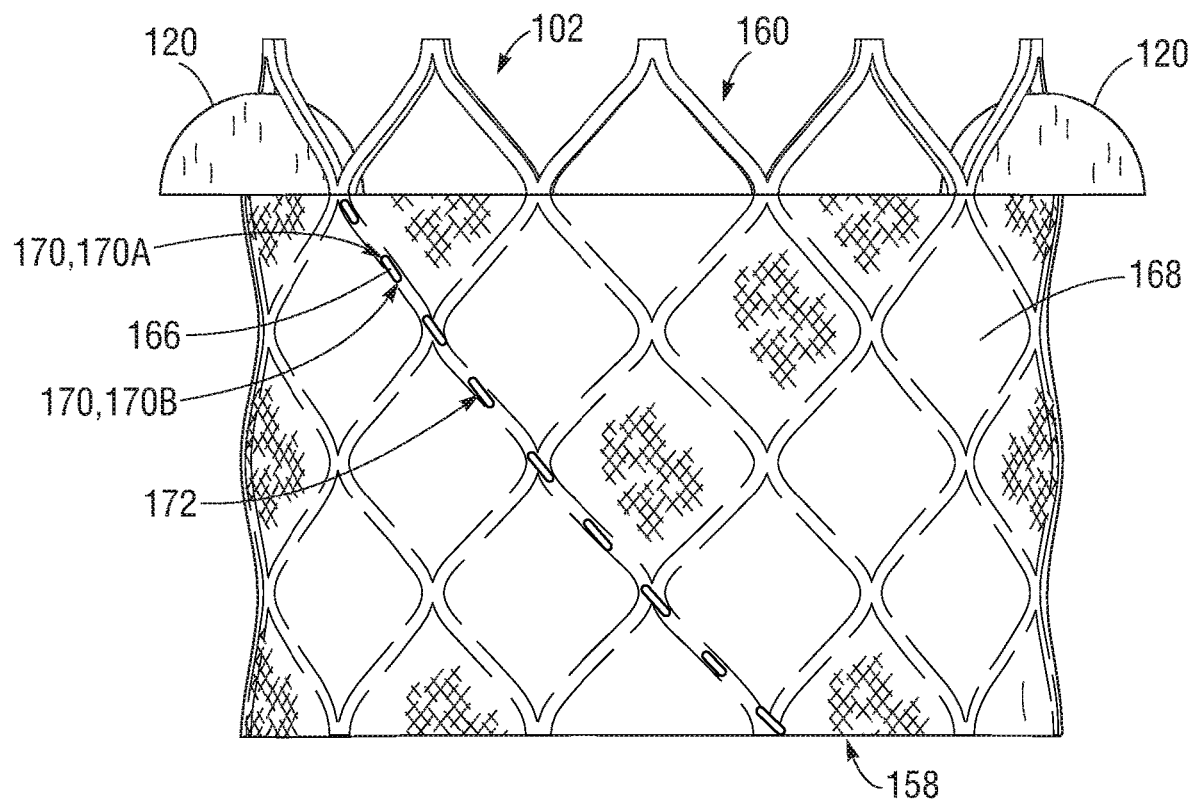
FIG. 11 is a side elevational view of a representative embodiment of a prosthetic valve including an outer skirt secured to a frame with a cord that also secures a leaflet-skirt assembly to the frame.

FIG. 1 illustrates a representative embodiment of a prosthetic heart valve 100, according to one embodiment. The illustrated valve is adapted to be implanted in the native aortic annulus although, in other embodiments, it can be adapted to be implanted in other native annuluses of the heart. The valve 100 illustrated in FIG. 1 includes a stent, or frame, 102, and a valvular structure 104. Certain embodiments can also include an outer skirt (e.g., a perivalvular leakage skirt or sealing member) secured to the outside of the frame, as shown in FIG. 11.

The valvular structure 104 can comprise three leaflets 106, collectively forming a leaflet structure, which can be arranged to collapse in a tricuspid arrangement. The lower edge of leaflet structure 104 desirably has an undulating, curved scalloped shape. For instance, with reference to FIGS. 1 and 6, each leaflet can include a main body portion 108 including curved side portions 110 and a lower portion 112 such that the leaflets 106 have a scalloped shape. By forming the leaflets with this scalloped geometry, stresses on the leaflets are reduced which, in turn, improves durability of the valve. Moreover, by virtue of the scalloped shape, folds and ripples at the belly of each leaflet (the central region of the main portions 108 of the leaflets), which can cause early calcification in those areas, can be eliminated or at least minimized. The scalloped geometry also reduces the amount of tissue material used to form the leaflet structure, thereby allowing a smaller, more even crimped profile at the inflow end of the valve. The leaflets 106 can be formed of pericardial tissue (e.g., bovine pericardial tissue), biocompatible synthetic materials, or various other suitable natural or synthetic materials as known in the art and described, for example, in U.S. Pat. No. 6,730,118, which is incorporated by reference herein.

The frame 102 can be formed from a plurality of angled strut members 114, and can have an inflow end 158 and an outflow end 160. The strut members 114 can be arranged to form a plurality of open cells 116 arranged in rows. The cells 116 can be configured to receive commissure structures 118 of the leaflet structure 104. For example, in the embodiment of FIG. 1, the uppermost row of cells 116 can be configured to receive commissure tabs 120 of the leaflets 106. The commissure tabs 120 can be secured (e.g., by suturing) to the strut members 114, thereby securing the leaflets to the frame and allowing the leaflets to open and close at the commissures in response to changes in blood pressure. In some configurations, the frame 102 can be formed with a plurality of specially-shaped and circumferentially spaced slots, or commissure windows (e.g., three commissure windows) that are adapted to mount the commissures of the valvular structure to the frame, as described, for example, in U.S. Patent Application No. 2012/0123529, which is incorporated herein by reference.

The frame 102 can be made of any of various suitable plastically-expandable materials (e.g., stainless steel, etc.) or self-expanding materials (e.g., Nitinol) as known in the art. When constructed of a plastically-expandable material, the frame 102 (and, thus, the valve 100) can be crimped to a radially compressed state on a delivery catheter and then expanded inside a patient by an inflatable balloon or equivalent expansion mechanism. When constructed of a self-expandable material, the frame 102 (and, thus, the valve 100) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 102 include, without limitation, stainless steel, a nickel based alloy (e.g., a cobalt-chromium or a nickel-cobalt-chromium alloy), polymers, or combinations thereof. In particular embodiments, frame 102 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 102 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Figure 6:
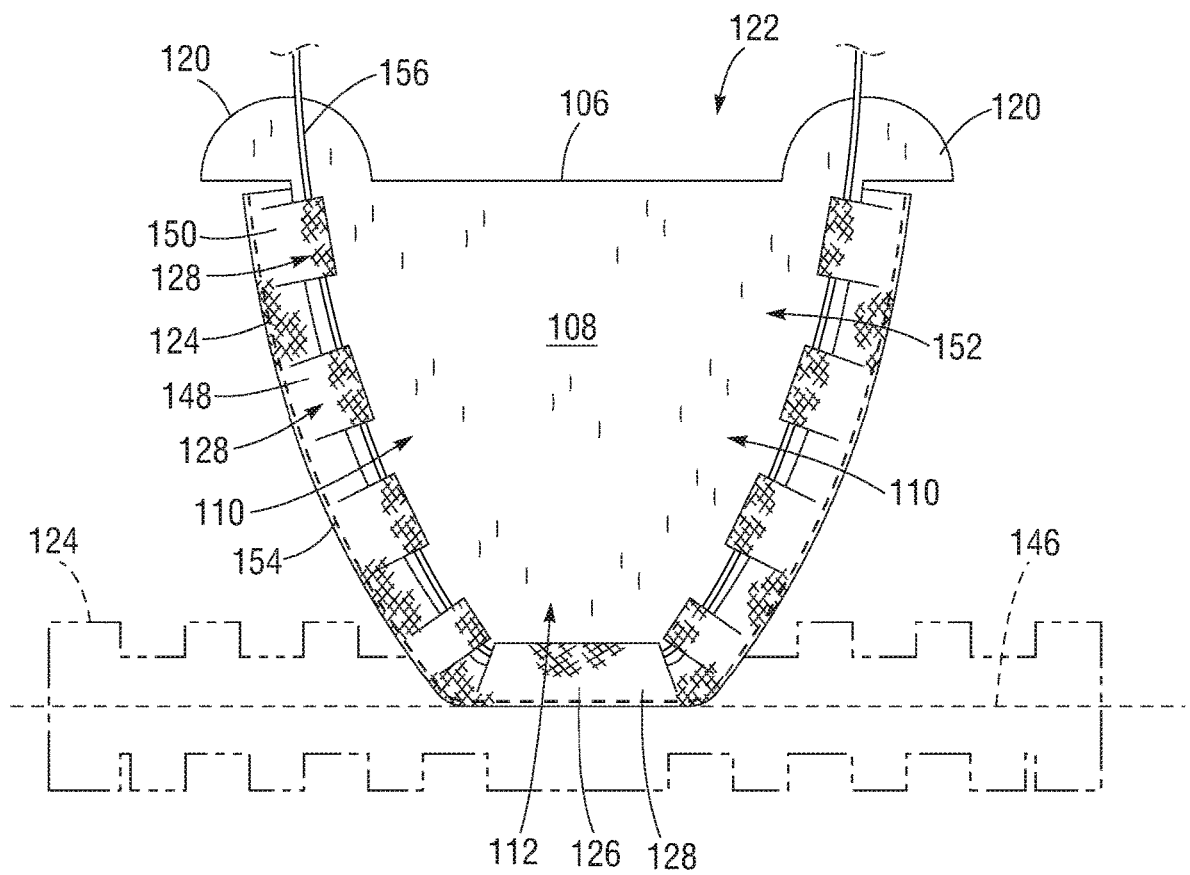
FIG. 6 is a side elevational view of a leaflet-skirt assembly.

Returning to the leaflet structure 104, the leaflet structure can comprise a plurality of leaflet-skirt assemblies 122. With reference to FIGS. 1 and 6, each leaflet 106 can include a peripheral leaflet skirt member 124 (also referred to as a connecting skirt) secured to the leaflet along the peripheral edges of the side portions 110 and the lower portion 112 of the main body 108 of the leaflets. The leaflet skirt 124 can then be wrapped around and secured to the strut members 114 of the frame to attach the leaflet to the frame.

Figure 2:
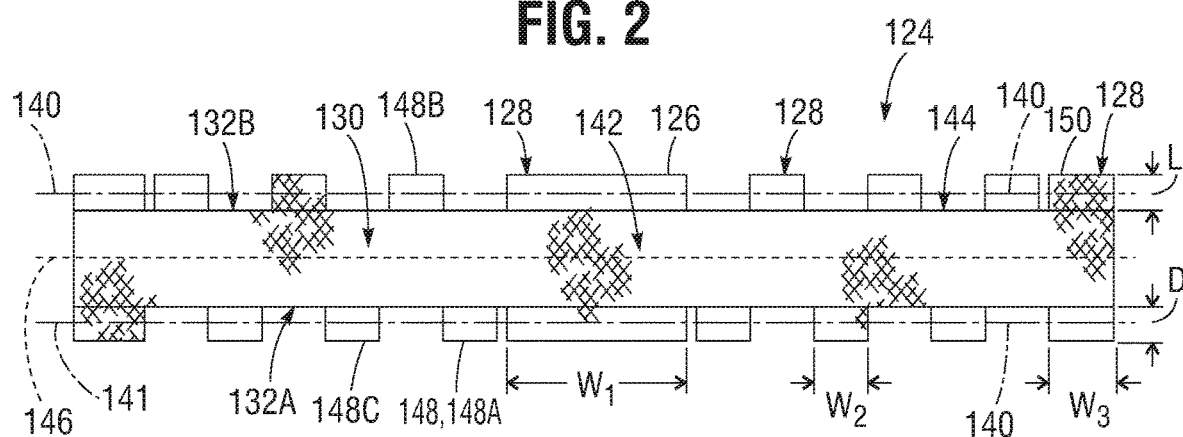
FIGS. 2-4 are plan views illustrating various embodiments of leaflet skirt members.

FIGS. 2-5 illustrate various embodiments of leaflet skirts 124 in greater detail. A representative leaflet skirt 124 is shown in FIG. 2, and can include a main body portion 130 having longitudinal edge portions 132A and 132B. A plurality of extension portions of varying sizes, such as first extension portions indicated at 126, can extend from the edge portions 132A, 132B of the main body 130, and can be separated from one another by gaps or recessed portions 144. The extension portions can include tubular portions 128 (e.g., located along the edges of the extension portions 126).

Figure 8:
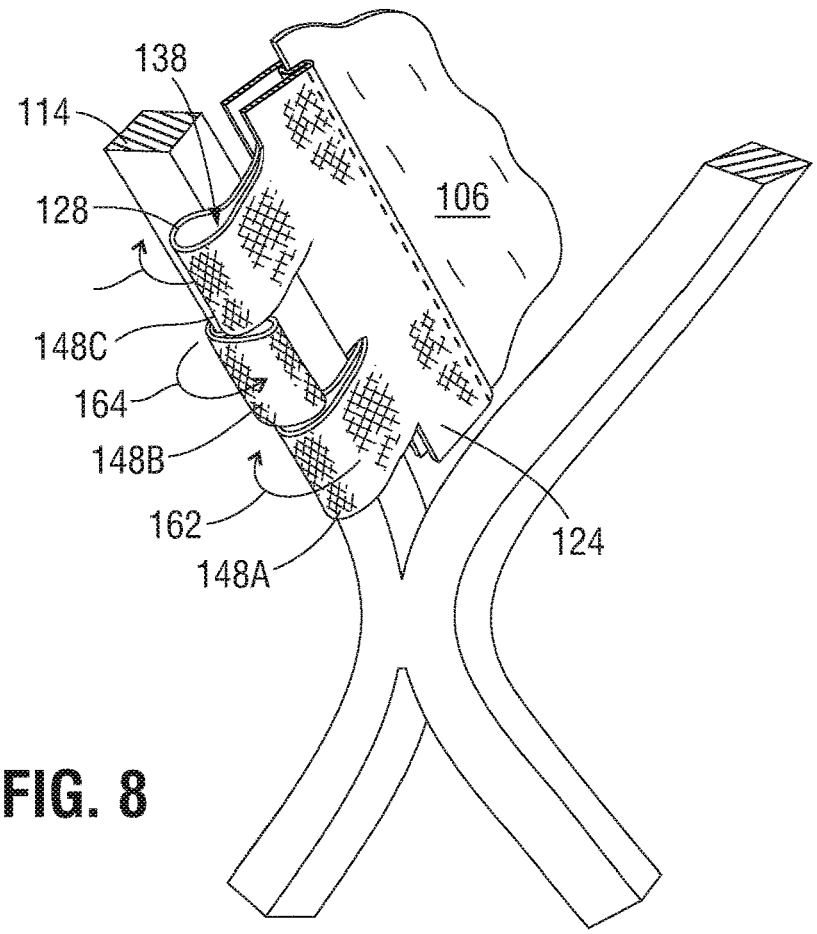
FIG. 8 is a perspective view of a portion of a leaflet-skirt assembly situated in a frame illustrating extension portions of a skirt member wrapped around strut members of the frame.

The tubular portions 128 can define respective lumens 138 (see FIGS. 8 and 9) which, when laid flat, can be substantially coaxial, as indicated by center lines 140 and 141.

Figure 3:
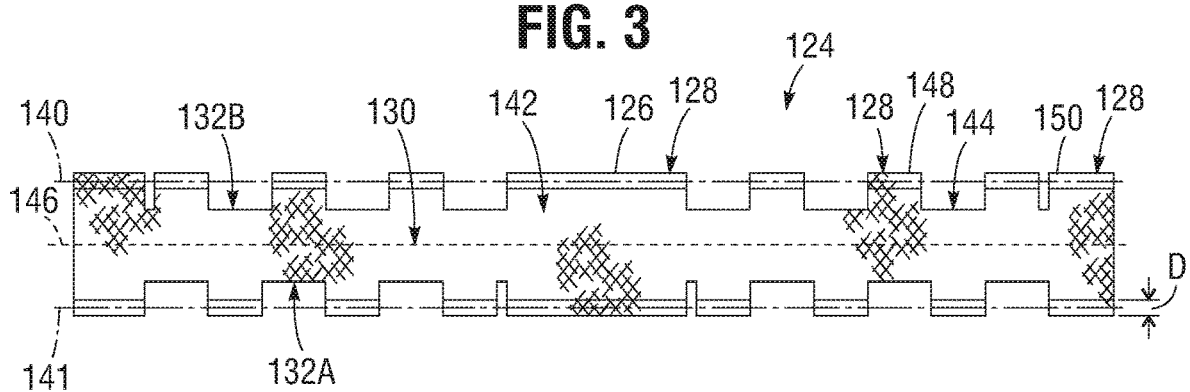
Figure 4:
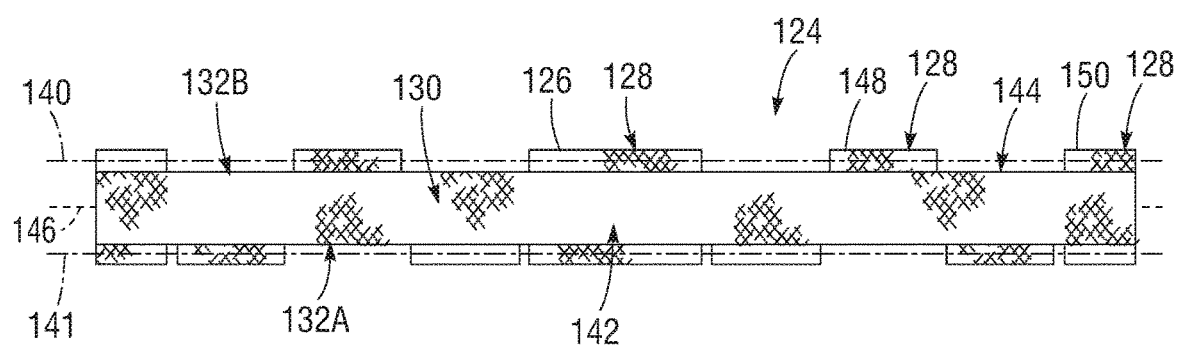
Figure 7:
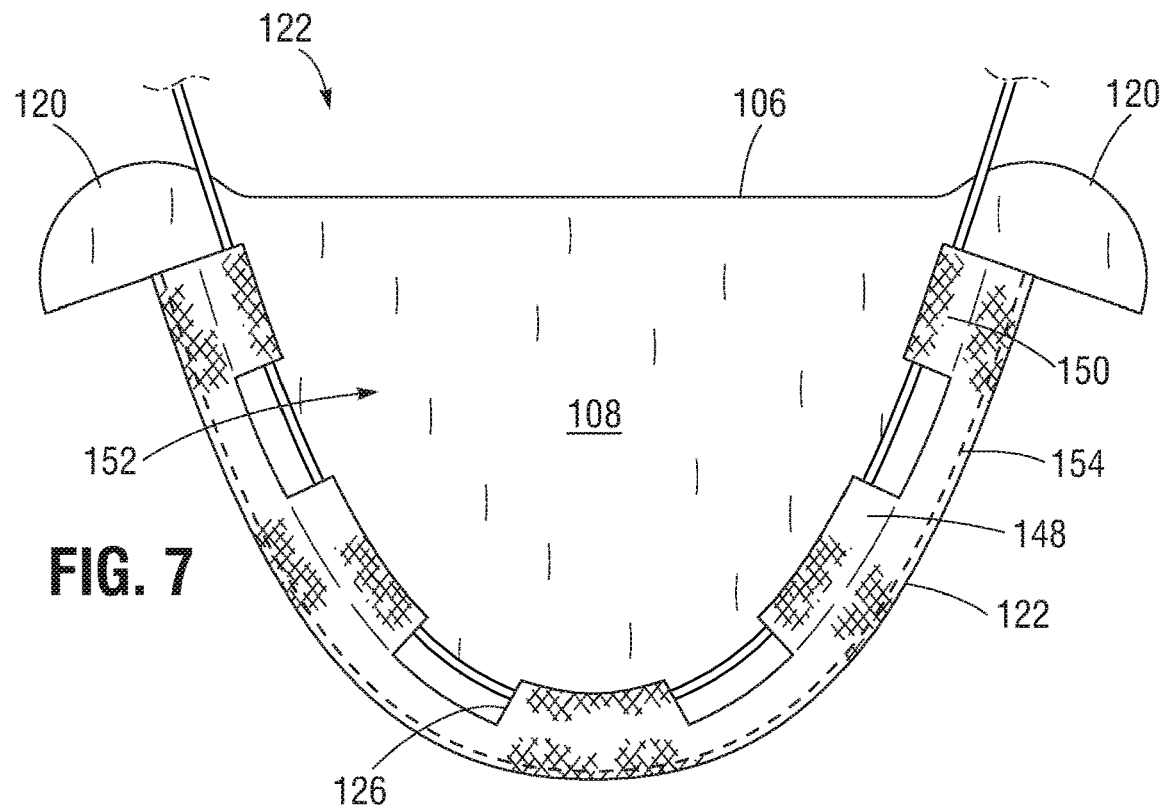
FIG. 7 is a side elevational view of another embodiment of a leaflet-skirt assembly.

The extension portions 126 can have width dimensions W extending in a direction parallel to the length of the leaflet skirt 124. The width dimensions W of the extension portions 126 can vary according to, for example, their location along the length of the skirt 124, the spacing between extension portions, the size and shape of the strut members of the frame, the size and shape of the cells 116 of the frame, and/or the size and shape of the leaflets 106. For example, the embodiments of FIGS. 2-4 can include first extension portions 126 having a first width dimension $W_1$, second extension portions 148 having a second width dimension $W_2$, and third extension portions 150 having a third width dimension $W_3$. In the embodiments of FIGS. 2 and 3, the width dimension $W_3$ of the third extension portions 150 is larger than the width dimension $W_2$ of the second extension portions, and the width $W_1$ of the first extension portions 126 is greater than both the widths $W_2$ and $W_3$. However, it should be understood that the various extension portions can have any suitable width dimensions. For example, FIG. 4 illustrates an alternative embodiment wherein the width of the second extension portions 148 is greater than the width of the third extension portions 150. In another embodiment illustrated in FIG. 7, the width dimensions of the first extension portions 126 and the width dimensions of the second extension portions 148 can be substantially equal.

Returning to FIG. 2, the first, second, and third extension portions 126, 148, 150 can also have length dimensions L. In the embodiments illustrated in FIGS. 2-4, all of the first, second, and third extension portions 126, 148, 150 have the same length dimension L. However, it should be understood that one or more of the first, second, and/or third extension portions can have different length dimensions L, as desired. In some embodiments, certain first, second, and/or third extension portions can also have different length dimensions L from other first, second, and/or third extension portions.

In the illustrated embodiments, the first extension portions 126 can be located at a central portion 142 of the leaflet skirt 124 such that when the skirt is attached to the leaflet 106, the first extension portions 126 are adjacent the lower portion 112 of the leaflet (see, e.g., FIGS. 1 and 6). In some embodiments, the width $W_1$ of the first extension portions 126 can be, for example, greater than 50%, greater than 60%, greater than 70%, or greater than 80% of the length of the lower portion 112 of the leaflet 106, as desired.

The second extension portions 148 can be arranged in an alternating fashion such that extension portions 148 located on side portion 132A are offset from extension portions 148 located on side portion 132B in a direction along a longitudinal axis 146 of the skirt, as illustrated in FIGS. 2-4. In some embodiments, the second extension portions 148 can be offset from one another along the side portions 132A, 132B by a distance less than, equal to, or greater than, the width dimension $W_2$, as desired. For example, with reference to FIG. 2, the extension portion 148B on side portion 132B can be offset from the extension portion 148A on side portion 132A by a distance approximately equal to the width dimension $W_2$ (measured from the center of one side portion to the center of the other side portion). Meanwhile, the extension portion 148C can be offset from the extension portion 148B by a distance greater than the width dimension $W_2$, such that there can be a gap or spacing between the adjacent edges of the side portions along the length of the skirt.

In some embodiments, the second extension portions 148 can be sized and spaced apart from one another along the length of the leaflet skirt such that one or more extension portions 148 are located within respective cells 116 of the frame 102 when the leaflet-skirt assembly 122 is situated in the frame. For example, in the embodiment of FIG. 1, the extension portions 148 are sized and spaced apart such that two extension portions 148 are located within each cell 116 along the side portions 110 of the leaflets 106. Alternatively, any suitable number of extension portions 148 can be located in the cells 116, such as three extension portions (see FIGS. 8 and 10) or more, or a single extension portion, as desired. This can facilitate accurate alignment of the leaflet-skirt assembly 122 within the frame 102 because the extension portions are pre-configured to align with the desired position of the leaflet-skirt assembly in the frame.

Returning to FIGS. 2-4, the leaflet skirt 124 can include third extension portions 150 located at the end portions of the leaflet skirt. In the illustrated configurations, the width dimensions $W_3$ of the third extension portions 150 can be greater than the width dimensions $W_2$ of the second extension portions 148 but less than the width dimensions $W_1$ of the first extension portions 126, although it should be understood that other configurations are possible. When the leaflet 106 and the skirt 124 are assembled together, the third extension portions 150 can be located adjacent (e.g., below) the commissure tabs 120 of the leaflet, as shown in FIGS. 1 and 6.

Referring still to FIGS. 2-4, the lumens 138 of the tubular portions 128 can have a diameter D. The diameter D of the lumens 138 of the tubular portions 128 can be varied according to, for example, the diameter of cords, sutures, threads, etc., that are to be threaded through the tubular portions 128, as further described below. For example, FIG. 2 illustrates an embodiment wherein a diameter D of the lumens 138 is substantially equal to a length L of the extension portions 148. In contrast, FIG. 3 illustrates an embodiment in which the diameter D of the lumens 138 is smaller than the length L of the extension portions 126.

Figure 5:
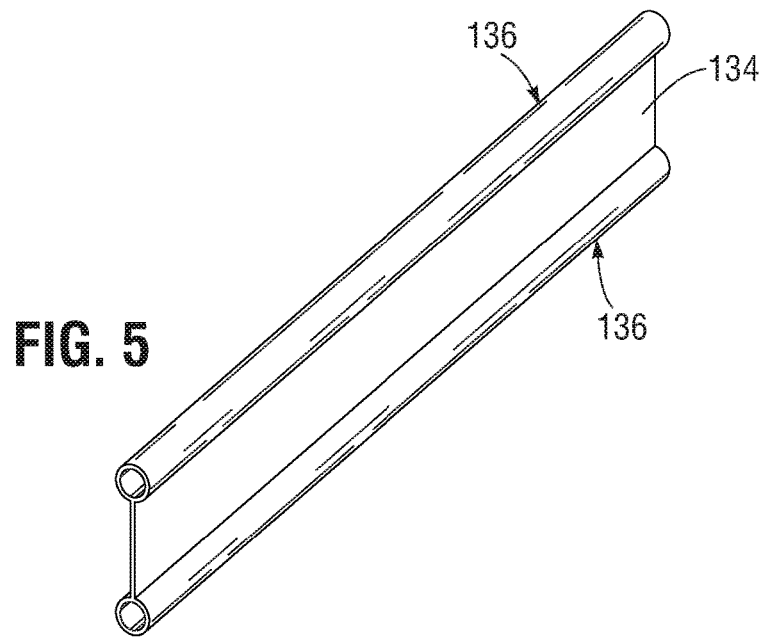
FIG. 5 is a perspective view of a representative embodiment of a fabric member including longitudinal tubes from which the skirt members of FIGS. 2-4 can be made.

Referring to FIG. 5, the leaflet skirt 124 can be made from a ribbon or strip 134 of material defining tubes or lumens 136 extending along side portions of the strip 134. The tubes 136 can be cut (e.g., by laser cutting) to form the first, second, and third extension portions 126, 148, 150 with the appropriate length, width, and spacing. The strip 134 and, hence, the leaflet skirt 124, can be made from any of various biocompatible materials with suitable flexibility and/or suture retention properties, including various woven fabrics such as gauze, polyethylene terephthalate (PET) fabric (e.g., Dacron®), polyester fabric, polyamide fabric, or any of various non-woven fabrics, such as felt. The skirt 124 can also be made from woven natural fibers such as silk, cotton, etc. Alternatively, the skirt 124 can also be made from any of various polymeric material films, such as PTFE, PET, polypropylene, polyamide, polyetheretherketone (PEEK), ultra high molecular weight polyethylene (UHMWPE) (e.g., Dyneema®), etc. The skirt can also be made from various composite materials, such as UHMWPE film reinforced with suture, such as Force Fiber® suture.

Turning now to assembly of the leaflet 106 and the leaflet skirt 124, the leaflet 106 can be positioned such that the lower portion 112 is adjacent the central portion 142 of the leaflet skirt 124, as shown in FIG. 6. The leaflet skirt 124 can then be folded about the peripheral edge of the lower portion 112 and the side portions 110 such that peripheral edge is positioned generally along the longitudinal axis 146 of the leaflet skirt. The extension portions 126, 148, 150 of the longitudinal edge portion 132A of the skirt can be disposed on an outward-facing surface 152 (e.g., the surface facing radially outward when the leaflet is positioned in the frame 102), and the extension portions 126, 148, 150 of the longitudinal edge portion 132B of the skirt can be disposed on an interior surface of the leaflet. The leaflet skirt 124 can then be sutured to the leaflet generally along the perimeter of the scalloped main body 108 of the leaflet as indicated by suture line 154 of FIGS. 1 and 6 to form the leaflet-skirt assembly 122. In some embodiments, a guide wire or cord or suture or thread 156 can be threaded through the lumens 138 of the tubular portions 128. The guide wire 156 can aid in positioning the skirt 124 on the leaflet 106, and can hold the skirt in place as it is sutured to the leaflet.

Figure 9:
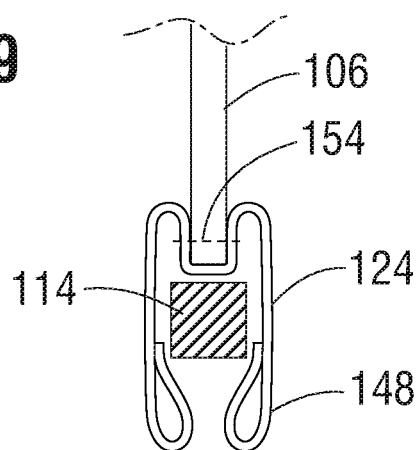
FIG. 9 is a cross-sectional view of the leaflet-skirt assembly and the frame illustrated in FIG. 8.

After the skirt 124 has been secured to the leaflet 106, the leaflet-skirt assembly 122 can be positioned inside the frame 102. The first extension portions 126 can be folded upwardly around the lower portion 112 of the leaflet 106. The second and third extension portions 148, 150 can extend through the cells 116 of the frame, and can be folded around the strut members 114. More specifically, with reference to FIGS. 8 and 9, adjacent sequential extension portions 148 along the longitudinal axis of the skirt member can be wrapped around the strut members 114 in opposite directions such that the respective tubular portions 128 are coaxially aligned with one another on the outside of the frame. For example, referring to FIG. 8, when viewed from the outflow end 160 of the frame, the extension portion 148A can be wrapped around the strut member in a clockwise direction indicated by arrow 162. Extension portion 148B can be wrapped around the strut member 114 in a counterclockwise direction, as indicated by arrow 164, and extension portion 148C can be wrapped around the strut member in the clockwise direction, as indicated by arrow 174. This pattern of wrapping the extension portions 148, 150 around the strut members in opposite directions can be repeated along the length of the side portions 110 of the leaflet 106. FIG. 9 illustrates a cross-sectional plan view through the strut member 114 of FIG. 8, and shows the leaflet skirt 124 folded around the edge of the leaflet 106, with the edge portions of the skirt then folded back toward the strut member such that the extension portions can be wrapped around the strut member.

Figure 10:
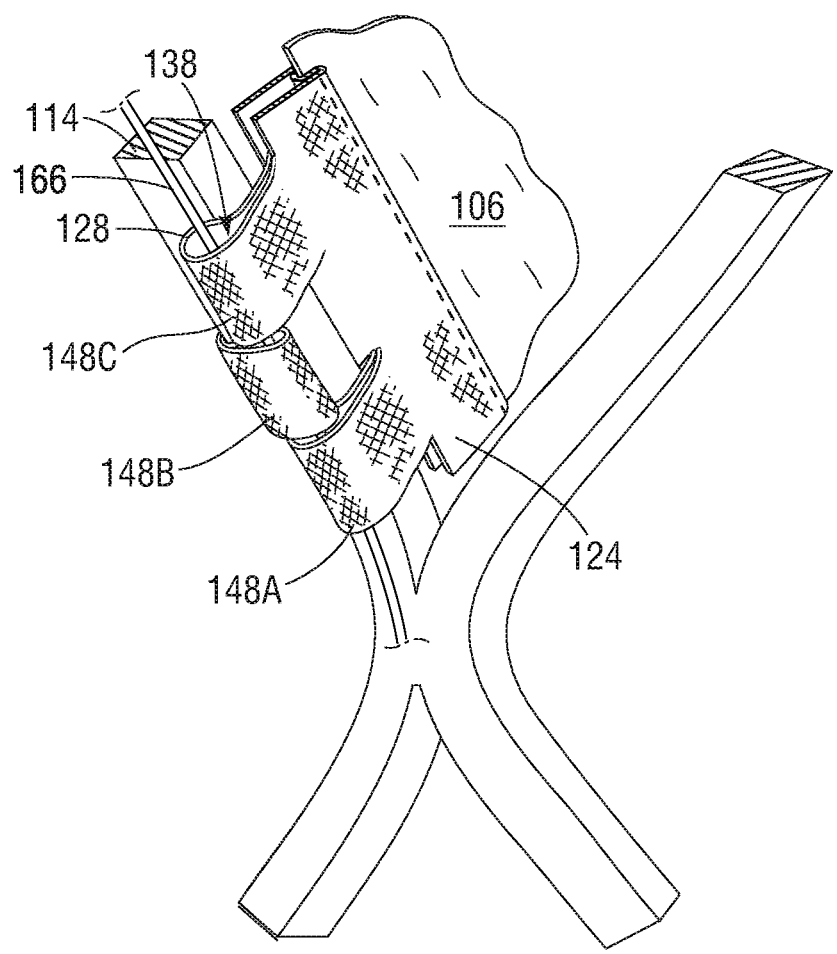
FIG. 10 is a perspective view of the assembly of FIG. 8 illustrating a cord threaded through the tubular portions of the skirt member.

When the extension portions 126, 148, 150 have been wrapped around the strut members in the desired manner, a guide wire or cord member (e.g., cord, suture, thread, etc.) 166 can be threaded through the tubular portions 128 of the extension portions 126, 148, 150 to secure the leaflet-skirt assembly 122 to the frame, as shown in FIGS. 1 and 10. For example, the cord member 166 can be threaded through the third extension portion 150 on one side of the skirt 124, through the second extension portions 148 and the first extension portion 126 on the outward-facing surface 152 of the leaflet, and then through the second extension portions and the third extension portion 150 on the opposite side of the skirt. In this manner, the cord member 166 can prevent the extension portions 126, 148, 150 from unwrapping from around the strut members 114. In some embodiments, the extension portion 126 on the inside of the frame can be held in place by the tension in cord 166. The extension portion 126 on the inside of the frame can also be secured to other fabric components of the valve, such as an inner skirt or an outer skirt (e.g., a PVL skirt) by, for example, sutures.

This process can be repeated for each leaflet-skirt assembly 122 to be placed in the frame, so that the frame includes the appropriate number of leaflets for the target heart valve (e.g., two leaflets arranged to collapse in a bicuspid arrangement for the mitral valve, three leaflets for the aortic valve, and three leaflets for the tricuspid valve). In alternative embodiments, the cord member 166 need not be threaded through either of the first extension portions 126. Rather, at least the first extension portion 126 located on the outward-facing surface 152 of the leaflet can be pinned and retained against the outward-facing surface of the leaflet by the strut members at the inflow end 158 of the frame.

After the cord members 166 have been threaded through the tubular portions 128, the end portions of the cord members 166, shown unsecured in FIG. 1 for purposes of illustration, can be secured or otherwise located so as not to interfere with implantation or operation of the prosthetic device. For example, the end portions of the cord members 166 can be tied to the strut members 114 of the frame, tied to one another, tied around or through the third extension portions 150, sutured to the leaflet skirt 124 other fabric components of the valve, and/or sutured to the leaflet 106, as desired.

Referring to FIG. 11, the cord members 166 can also be used to secure an outer skirt to the frame, such as perivalvular leakage (PVL) skirt 168. For example, in a representative embodiment, the PVL skirt 168 can include preformed slits or openings 170 that are located between extension portions 126, 148, 150 of the leaflet skirt 124 when the PVL skirt is placed around the frame. In the embodiment illustrated in FIG. 11, the preformed openings 170 can be arranged in pairs, such as the exemplary pair of openings 170A, 170B. In this manner, as the cord member 166 is threaded through the tubular portions 128 of the leaflet skirt 124, the cord member can also be threaded through the first preformed opening 170A and back through the second preformed opening 170B of the PVL skirt, before being threaded through the tubular portion of the next extension portion of the leaflet skirt. As shown in FIG. 11, the cord member 166 can form a "stitch line" 172 along the PVL skirt 168 corresponding to the location of the side portion 110 of the respective leaflet 106. When two or more leaflet-skirt assemblies 122 are placed in the frame, each of the respective cord members used to secure the leaflet-skirt assemblies to the frame can also be used to secure the PVL skirt 168 to the frame.

Figure 15:
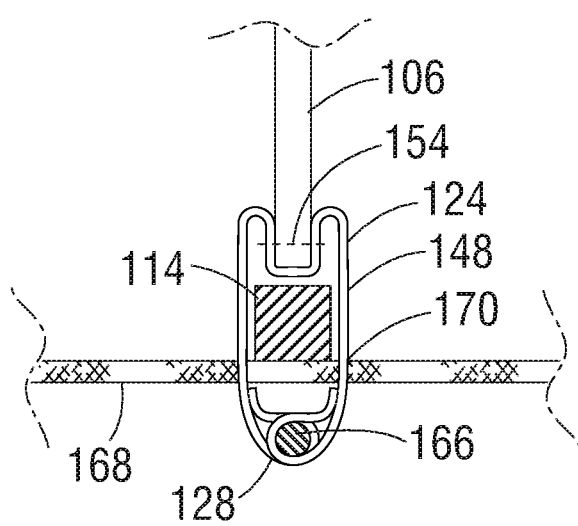
FIG. 15 is a cross-sectional view of the leaflet-skirt assembly and the frame of FIG. 10 illustrating tubular portions of the extension portions extending through slits in an outer skirt such that the outer skirt is secured to the frame by the cord threaded through the tubular portions.

In another embodiment illustrated in FIG. 15, the openings 170 can be slits sized and located such that the tubular portions of the various extension portions can be inserted through the respective slits in the PVL skirt. For example, FIG. 15 illustrates the tubular portions 128 of the extension portions 148 extending through the slits 170. The cord member 166 can then be threaded through the tubular portions on the outside of the PVL skirt to secure the PVL skirt to the frame.

The leaflet skirt and leaflet-skirt assembly embodiments described herein can provide significant advantages over known prosthetic device assembly techniques. For example, the leaflet skirt 124 can provide strength and reinforcement to the edges of the leaflet that is typically provided by a reinforcing strip, while at the same time providing a way to quickly and accurately align the resulting leaflet-skirt assembly with the frame 102. Because the various extension portions of the leaflet skirt 124 are configured to be aligned with specified cells of the frame, the leaflet-skirt assembly can be quickly and accurately placed at the specified location within the frame. The leaflet-skirt assembly can also be quickly and reliably secured to the strut members of the frame, without requiring any sutures. This can significantly simplify the assembly process, reduce the cost and time required to assemble a valve, and increase yield by reducing positioning errors during the suturing process.

Figure 12:
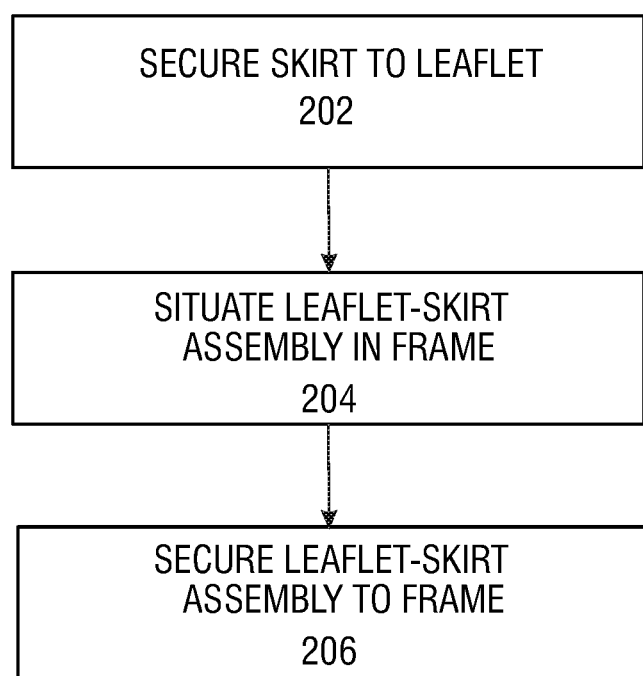
FIG. 12 is a process flow diagram illustrating a representative method of making a leaflet-skirt assembly and situating the assembly in a frame.

FIG. 12 is a process flow diagram illustrating a representative method of making a leaflet-skirt assembly and placing the leaflet-skirt assembly in a frame of a prosthetic device. At block 202, a skirt member can be secured to a valve leaflet to form a leaflet-skirt assembly. The skirt member can include first and second longitudinal edge portions and a plurality of extension portions along at least one of the longitudinal edge portions. The extension portions can define tubular portions.

At block 204, the leaflet skirt assembly can be situated in a frame.

At block 206, the extension portions of the skirt member can be wrapped around strut members of the frame to secure the leaflet-skirt assembly to the frame.

Figure 13:
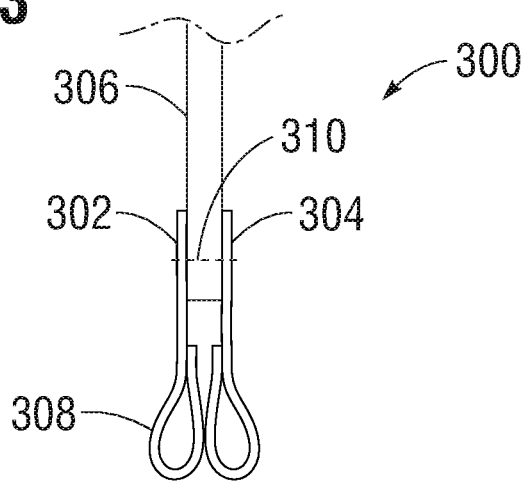
FIG. 13 is a cross-sectional view of an alternative embodiment of a leaflet-skirt assembly including two skirt members.
Figure 14:
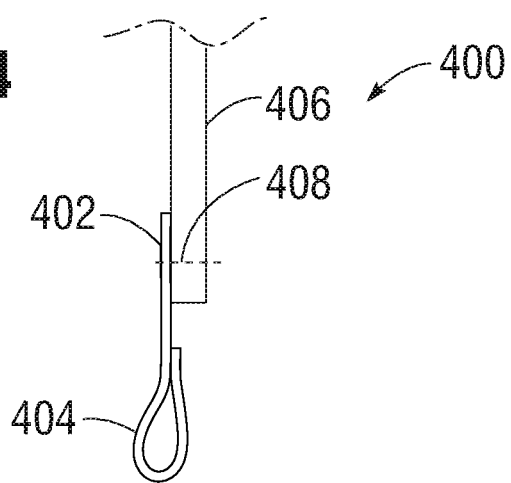
FIG. 14 is a cross-sectional view of an alternative embodiment of a leaflet-skirt assembly including a skirt member secured on one side of a leaflet.

FIGS. 13 and 14 illustrate alternative embodiments of the leaflet-skirt assembly. FIG. 13 illustrates a leaflet-skirt assembly 300 in which the leaflet skirt comprises two separate pieces of material 302, 304 secured on opposite sides of the leaflet 306 by suturing 310, or any other suitable fixation method. The respective skirt members 302, 304 can include extension portions 308 located on respective longitudinal edge portions of the skirt members similar to those described above with respect to the embodiment of FIG. 1.

FIG. 14 illustrates another embodiment 400 in which the leaflet skirt comprises a single piece of material 402 including a plurality of extension portions 404. The skirt 402 is secured to one side of the leaflet 406 by suturing 408.

Figure 16:
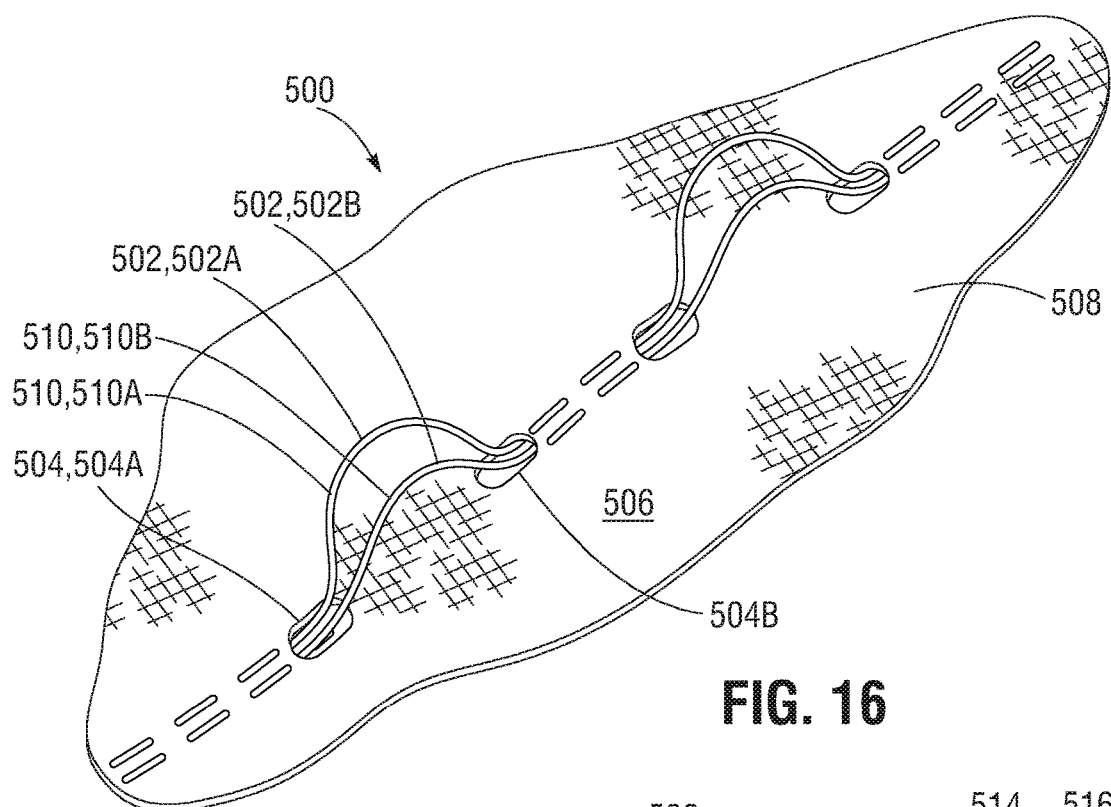
FIG. 16 is a perspective detail view of a portion of a skirt member including suture threads extending between openings in the skirt member to form loop portions.
Figure 17:
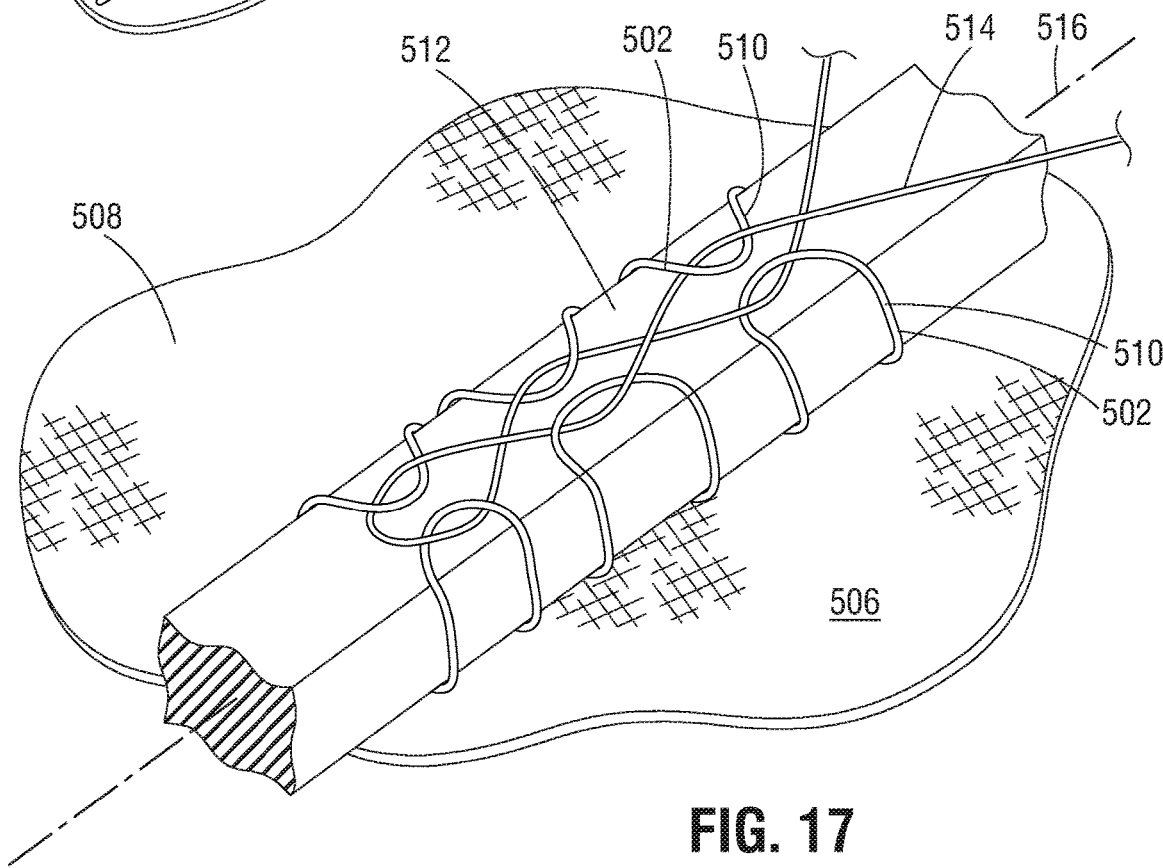
FIG. 17 is a perspective detail view illustrating the skirt member of FIG. 16 secured to a strut member of a frame by wrapping the loop portions around the strut member and threading a cord through the loop portions.

FIGS. 16 and 17 illustrate another method of securing various components of a prosthetic heart valve to a frame of the valve. FIG. 16 illustrates a representative example wherein a pair of threads, sutures, or chords 502 are inserted through openings 504 defined in a skirt 506. The openings 504 are spaced apart from one another along an axis corresponding to, for example, a longitudinal axis of a strut member (see FIG. 17) that will be adjacent the openings when the skirt is secured to a frame.

The skirt member 506 can define a primary surface 508 and a secondary surface opposite the primary surface. The threads 502 can be threaded through the openings 504 such that they form curved extension portions configured as loop portions 510 between successive openings on the primary surface 508 of the skirt member. For example, with reference to representative loop portion 510A, the thread 502A can pass through the opening 504A to the primary surface side of the skirt member 506 and pass through the opening 504B to the secondary surface side of the skirt member such that loop portion 510A originates at opening 504A and terminates at opening 504B. Alternatively, the loop portions can originate and terminate from the same opening, as desired.

As stated above, a pair of threads 502 can be inserted through the openings 504 such that the loop portions 510 are formed in pairs. As illustrated in FIG. 17, when the skirt member 506 is secured to a strut member 512 of a frame, the skirt member can be positioned such that the primary surface 508 is adjacent the strut member and the strut member is located between the loop portions 510 of each respective pair of loops. A thread or cord member 514 can then be threaded through the loop portions 510 to secure the skirt member 506 to the frame. For example, as shown in FIG. 17, the cord member 514 can be threaded through the loop portions 510 in a crisscross pattern, with the cord passing through a loop portion on one side of the strut member 512, extending across a longitudinal axis 516 of the strut member, and passing through a loop portion on the opposite side of the strut member, etc.

When the cord member 514 has been threaded through a final selected loop portion (for example, the last loop portion on one side of the strut member), the cord member can be threaded through the corresponding loop portion on the opposite side of the strut member 512, and the threading process can be repeated along the strut member in the opposite direction such that the cord member overlaps or crosses itself along the length of the strut member between pairs of loop portions 510. In this manner, the loop portions 510 can be tied or laced to the strut member with the cord member 514 in a manner analogous to shoe laces. This process can be repeated for each respective strut member 512 to which the skirt member 506 is to be secured. In this manner, the skirt member 506 can be secured to the frame without forming individual stitches extending around the struts while the skirt is placed on the frame. Since the loop portions 510 are pre-formed prior to placing the skirt against the frame, substantial time can be saved in the manufacture of the prosthetic valve.

The above securing technique can be applicable to any suitable valve component on which loop portions, such as the loop portions 510, can be created. For example, the skirt member 506 can be an outer skirt, such as a PVL skirt, or an inner skirt. The threads 502 and/or the cord member 514 can be, for example, suture, or threads formed from any of various natural or synthetic fibers, or polymeric materials.

Figure 18:
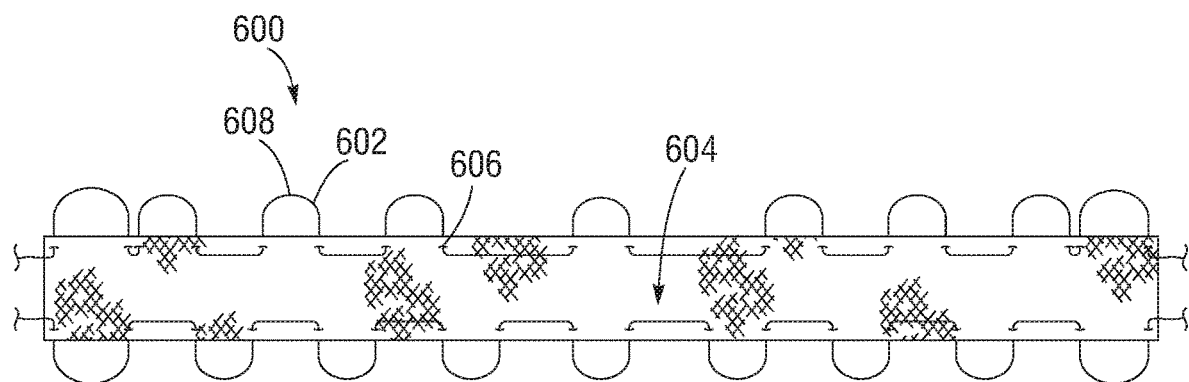
FIG. 18 is a plan view of another embodiment of a leaflet skirt member including loop portions formed with suture threads.

The attachment technique illustrated in FIGS. 16 and 17 can also be applicable to the leaflet-skirt assemblies described above with respect to FIGS. 1-15. For example, FIG. 18 illustrates an exemplary embodiment of a leaflet skirt member 600 including a plurality of extension portions configured as loop portions 602 formed from threads 608. The leaflet skirt 600 can have a first surface 604 and a second surface opposite the first surface, and can define a plurality of openings 606 spaced apart from one another in a direction along a longitudinal axis of the leaflet skirt. Threads 608 can be threaded through the openings 606 such that the threads form the loop portions 602 on the second surface.

Figure 19:
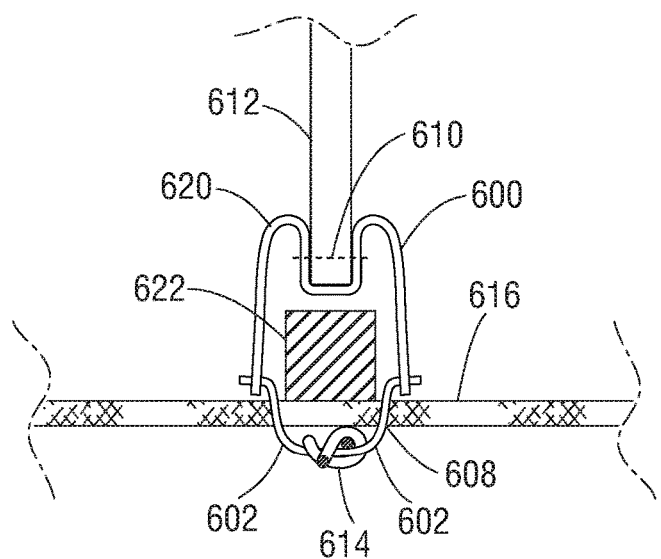
FIG. 19 is a cross-sectional view of a leaflet-skirt assembly including the leaflet skirt member of FIG. 18 secured to strut member of a frame and an outer skirt.

Referring to FIG. 19, the leaflet skirt 600 can then be folded about and secured (e.g., by suturing 610) to the edge of a leaflet 612 to form a leaflet-skirt assembly 620. The leaflet-skirt assembly 620 can be secured to a strut member 622 of a frame by a cord member 614 threaded through the loop portions 602 in a crisscross pattern, as described above. In the illustrated embodiment, this technique can also be used to secure an outer skirt member 616 to the frame. For example, the loop portions 602 can be inserted through openings 618 defined in the skirt member 616, and the cord member 614 can be threaded through the loop portions on a radially outward surface of the skirt member 616, as shown in FIG. 19.

Figure 20:
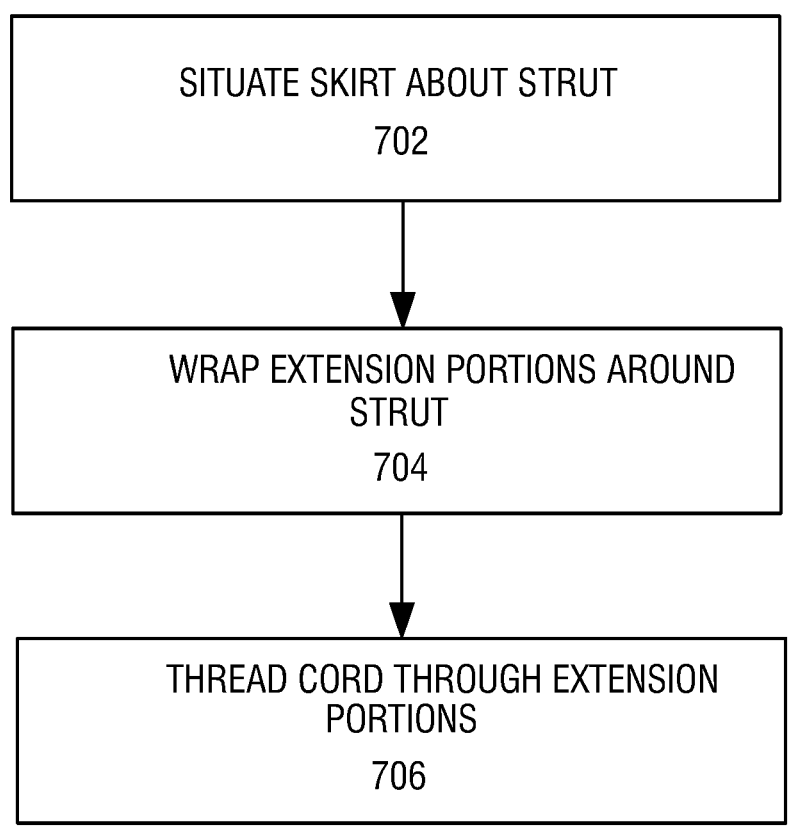
FIG. 20 is a process flow diagram illustrating a representative method of securing a skirt member to a frame of a prosthetic valve.

FIG. 20 illustrates another representative method of securing a skirt member to a frame of a prosthetic valve. At block 702, a skirt member can be situated adjacent a strut member of a frame of a prosthetic valve. The skirt member can include a plurality of extension portions, such as the extension portions 148 formed from the material of the skirt member 124, or extension portions configured as loop portions and formed with suture threads.

At block 704, at least a portion of the plurality of extension portions can be wrapped around the strut member.

At block 706, a cord member can be threaded through the extension portions wrapped around the strut member to secure the skirt member to the frame.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. An implantable prosthetic valve that is radially collapsible to a collapsed configuration and radially expandable to an expanded configuration, the prosthetic valve comprising:
   an annular frame including a plurality of angled strut members;
   a plurality of leaflets disposed within the frame and secured to the frame;
   a skirt member secured to the frame, the skirt member having a longitudinal axis aligned with an edge portion of a leaflet, the skirt member including a plurality of extension portions wrapped around at least one strut member adjacent the extension portions; and
   a cord member threaded through at least a portion of the plurality of extension portions in a direction along the longitudinal axis of the skirt member to secure the skirt member to the at least one strut member.

2. The prosthetic valve of claim 1, wherein the skirt member is secured to the edge portion of the leaflet.

3. The prosthetic valve of claim 2, wherein the skirt member comprises first and second longitudinal edge portions, and the plurality of extension portions are located on at least one of the longitudinal edge portions.

4. The prosthetic valve of claim 3, wherein the skirt member is folded about the edge portion of the leaflet such that the first and second longitudinal edge portions extend from opposite sides of the leaflet.

5. The prosthetic heart valve of claim 2, wherein sequential extension portions along the longitudinal axis of the skirt member are wrapped around the at least one strut member in opposite directions.

6. The prosthetic heart valve of claim 5, wherein:
   the extension portions define respective openings; and
   the extension portions are wrapped around the at least one strut member such that the at least one strut member is outside the bounds of the openings.

7. The prosthetic valve of claim 6, wherein the extension portions define tubular portions coaxially aligned with each other on the outside of the frame.

8. The prosthetic valve of claim 2, wherein the skirt member is secured to the valve leaflet by suturing.

9. The prosthetic valve of claim 2, further comprising two leaflets and associated skirts members configured to collapse in a bicuspid arrangement, or three leaflets and associated skirt members configured to collapse in a tricuspid arrangement.

10. The prosthetic valve of claim 1, further comprising an outer skirt secured to the frame with the cord member.

11. The prosthetic valve of claim 10, wherein at least a portion of the plurality of extension portions are inserted through openings defined in the outer skirt, and the cord member is threaded through the extension portions extending through the openings to secure the outer skirt to the frame.

12. The prosthetic valve of claim 1, wherein the extension portions are loop portions formed from one or more sutures inserted through openings defined in the skirt member.

13. The prosthetic valve of claim 12, wherein the loop portions are spaced apart from one another in a direction along a longitudinal axis of the at least one strut member.

14. The prosthetic valve of claim 12, wherein the loop portions are arranged in pairs, and the at least one strut member is located between the respective loop portions of at least one pair of loop portions.

15. A method, comprising:
   situating a skirt member adjacent a strut member of an annular frame of a prosthetic valve, the skirt member including a plurality of extension portions and a longitudinal axis aligned with an edge portion of a leaflet;
   wrapping at least a portion of the plurality of extension portions around the strut member;
   threading a cord member through the extension portions wrapped around the strut member in a direction along the longitudinal axis of the skirt member to secure the skirt member to the frame; and repeating the situating, the wrapping, and the threading such that the prosthetic valve includes a plurality of leaflets disposed within the frame and secured to the frame.

16. The method of claim 15, wherein the wrapping further comprises wrapping sequential extension portions around the strut member in opposite directions such that respective openings defined by the extension portions are coaxially aligned with one another on the outside of the frame.

17. The method of claim 15, further comprising securing the skirt member to the edge portion of the leaflet by suturing.

18. An implantable prosthetic valve that is radially collapsible to a collapsed configuration and radially expandable to an expanded configuration, the prosthetic valve comprising:
   an annular frame including a plurality of angled strut members;
   a plurality of leaflets disposed within the frame and secured to the frame;
   a skirt member secured to an edge portion of a leaflet of the plurality of leaflets such that a longitudinal axis of the skirt member is aligned with the edge portion of the leaflet, the skirt member having first and second longitudinal edge portions and a plurality of extension portions on at least one of the longitudinal edge portions, the extension portions defining tubular portions, at least a portion of the extension portions of the skirt member being wrapped around at least one strut member; and
   a cord member threaded through at least a portion of the tubular portions in a direction along the longitudinal axis of the skirt member to secure the leaflet and the skirt member to the frame.

19. The prosthetic heart valve of claim 18, wherein the extension portions of the skirt member are wrapped around the at least one strut member in opposite directions such that the tubular portions are coaxially aligned with each other on the outside of the frame.

20. The method of claim 19, further comprising securing an outer skirt to the frame with the cord member.

* * * * *